US007285297B1

(12) United States Patent
Waggle et al.

(10) Patent No.: US 7,285,297 B1
(45) Date of Patent: Oct. 23, 2007

(54) METHOD OF REDUCING LOW DENSITY LIPROPROTEIN CHOLESTEROL CONCENTRATION

(75) Inventors: Doyle H. Waggle, Creve Coeur, MO (US); Susan M. Potter, Ellisville, MO (US); Edna C. Henley, Athens, GA (US)

(73) Assignee: Archer-Daniels-Midland Company, Decatur, IL (US)

( * ) Notice: Subject to any disclaimer, the term of this patent is extended or adjusted under 35 U.S.C. 154(b) by 532 days.

(21) Appl. No.: 10/461,751

(22) Filed: Jun. 13, 2003

Related U.S. Application Data

(62) Division of application No. 09/826,346, filed on Apr. 4, 2001, now Pat. No. 6,579,534, which is a division of application No. 09/298,528, filed on Apr. 23, 1999, now Pat. No. 6,544,566.

(51) Int. Cl.
*A01N 65/00* (2006.01)
*G01N 31/00* (2006.01)
(52) U.S. Cl. .................................. 424/757; 436/13
(58) Field of Classification Search ................ None
See application file for complete search history.

(56) References Cited

U.S. PATENT DOCUMENTS

| 3,870,805 A | 3/1975 | Haynes et al. ............... 426/148 |
| 4,157,984 A | 6/1979 | Zilliken ....................... 252/407 |
| 4,265,824 A | 5/1981 | Koskenniska et al. . 260/397.25 |
| 4,298,539 A | 11/1981 | Koskenniska .......... 260/397.25 |
| 4,428,876 A | 1/1984 | Iwamura .................. 260/123.5 |
| 4,889,921 A | 12/1989 | Diosady et al. ............. 530/377 |
| 5,141,746 A | 8/1992 | Fleury et al. ............ 424/195.1 |
| 5,320,949 A | 6/1994 | Shen ........................ 435/68.1 |
| 5,352,384 A | 10/1994 | Shen .......................... 252/398 |
| 5,506,211 A | 4/1996 | Barnes et al. .................. 514/27 |
| 5,516,528 A | 5/1996 | Hughes et al. ............... 424/464 |
| 5,569,459 A | 10/1996 | Shlyankevich ........... 424/195.1 |
| 5,589,182 A | 12/1996 | Tashiro et al. ............... 424/423 |
| 5,637,561 A | 6/1997 | Shen et al. ..................... 514/2 |
| 5,637,562 A | 6/1997 | Shen et al. ..................... 514/2 |
| 5,654,011 A | 8/1997 | Jackson et al. ............. 424/514 |
| 5,670,632 A | 9/1997 | Chaihorsky ..................... 536/8 |
| 5,679,806 A | 10/1997 | Zheng et al. ................ 549/403 |
| 5,726,034 A | 3/1998 | Bryan et al. ................ 435/68.1 |
| 5,763,389 A | 6/1998 | Shen et al. ..................... 514/2 |
| 5,821,361 A | 10/1998 | Waggle et al. ............... 514/182 |
| 5,827,682 A | 10/1998 | Bryan et al. ................ 435/68.1 |
| 5,830,887 A | 11/1998 | Kelly ......................... 514/182 |
| 5,851,792 A | 12/1998 | Shen et al. ................ 435/68.1 |
| 5,855,892 A | 1/1999 | Potter et al. ............. 424/195.1 |
| 6,113,972 A | 9/2000 | Corliss et al. .............. 426/613 |
| 6,136,349 A | 10/2000 | Karppanen et al. ............ 426/2 |
| 6,413,557 B1 * | 7/2002 | Lee ............................ 424/757 |

FOREIGN PATENT DOCUMENTS

| EP | 647408 A1 | 4/1995 |
| JP | 48010076 A | 7/1974 |
| JP | 74027872 B | 7/1974 |
| JP | 59-085265 A | 5/1984 |
| JP | 59-232052 A | 12/1984 |
| JP | 62-036163 A | 2/1987 |
| JP | 62126186 A | 6/1987 |
| JP | 63245648 A | 10/1988 |
| JP | 1-258669 | 10/1989 |
| JP | 21-60722 A | 6/1990 |
| JP | 30-47049 A | 2/1991 |
| JP | 40-36242 A | 2/1992 |
| JP | 04-266898 A | 9/1992 |
| JP | 4-283518 A1 | 10/1992 |
| JP | 5170756 A | 7/1993 |
| JP | 53-28929 A | 12/1993 |

(Continued)

OTHER PUBLICATIONS

*Determination of isoflavones in soybean flours, protein concentrates, and isolates*, Eldridge, J. Agric. Food Chem., vol. 30, pp. 353-355 (1982).

(Continued)

*Primary Examiner*—David M. Naff
*Assistant Examiner*—Deborah K. Ware
(74) *Attorney, Agent, or Firm*—Kirkpatrick & Lockhart Preston Gates Ellis LLP

(57) ABSTRACT

The present invention is a composition comprising a plant sterol and a soy protein material and/or and isoflavone selected from genistein, daidzein, glycitein, biochanin A, formononetein, and their naturally occurring glycosides, where the plant sterol comprises at least 0.49% of the composition, by weight. The present invention is also a method for decreasing the blood concentration of total and LDL cholesterol in a human in which a plant sterol and a soy protein material and/or an isoflavone are co-administered to the human, where the plant sterol comprises at least 0.49%, by weight, of the combined weight of the plant sterol and the soy protein material and/or the isoflavone. The present invention is also a method for preventing or minimizing the development of atherosclerosis in a human in which a plant sterol and a soy protein material and/or an isoflavone are co-administered to the human, where the plant sterol comprises at least 0.49%, by weight, of the combined weight of the plant sterol and the soy protein material and/or the isoflavone.

3 Claims, 3 Drawing Sheets

FOREIGN PATENT DOCUMENTS

| | | |
|---|---|---|
| JP | 40-34526 B | 8/1994 |
| JP | 59-137421 A | 8/1994 |
| JP | 6287554 A | 10/1994 |
| JP | 8214787 A | 8/1996 |
| JP | 82-83283 A | 10/1996 |
| JP | 90-23822 A | 1/1997 |
| WO | WO93/23069 | 11/1993 |
| WO | WO96/10341 A1 | 4/1996 |
| WO | WO97/07811 | 3/1997 |
| WO | WO 00/30663 | 6/2000 |
| WO | WO 00/30665 | 6/2000 |

OTHER PUBLICATIONS

*Objectionable Flavor of Soy Milk Developed during the Soaking of Soybeans and its Control*, Matsurra, Obata, Fukushima, *J. Food Science*, vol. 54, No. 3, pp. 602-605 (1989).
*Isoflavone Content in Commercial Soybean Foods*, Wang and Murphy, *J. Agric. Food Chem.*, vol. 42, No. 8, pp. 1666-1673 (1994).
*Control of Serum Lipids with Soy Protein*, Erdman, *New England J. of Med.*, vol. 333, No. 5, pp. 313-315 (Aug. 3, 1995).
*Soy in the Spotlight*, Kuhn, *Food Process.*, vol. 57, No. 5, pp. 52-58 (1996).
*Studies on the Mechanism of the Cholesterol Lowering Activity of Soy Proteins*, Lovati et al., *Nutr. Metab. Cardiovasc. Disc.*, vol. 1, pp. 18-24 (1991).
*Quantitation of Phytoestrogens in Legumes by HPLC*, Franke et al., *J. Agric. Food Chem.*, vol. 42, pp. 1905-1913 (1994).
*Genistein, Daidzein, and Their β-Glycoside Conjugates: Antitumor Isoflavones in Soybean Foods from American and Asian Diets*, Coward et al., *J. Agric. Food Chem.*, 41:1961-67; (1993).
*Dietary Carbohydrates and Low Cholesterol Diets: Effects on Serum Lipids of Man*; Hodges et al.; *The American Journal of Clinical Nutrition*; vol. 20, No. 2, pp. 198-208; (Feb. 1967).
*Meta-analysis of the Effects of Soy Protein Intake on Serum Lipids*, Anderson, Johnstone, and Cook-Newell, *New England J. of Med.*, vol. 333, No. 5, pp. 276-282 (Aug. 3, 1995).
*Soy Isoflavones Enhance Coronary Vascular Reactivity in Atherosclerotic Female Macaques*, Honore, Williams, Anthony and Clarkson, *Fertil. Steril.*, vol. 67, No. 1, pp. 148-154 (Jan. 1997).
*Soy Protein and Serum Lipids*, Potter; *Curr. Opin. Lipidol.*, vol. 7, No. 4, pp. 260-264 (Aug. 1996).
*Soybean Isoflavones Improve Cardiovascular Risk Factors Without Affecting the Reproductive System of Peripubertal Rhesus Monkeys*, Anthony, Clarkson, Hughes, Morgan and Burke, *J. Nutr.*, vol. 126, No. 1, pp. 43-50 (Jan. 1996).
*Oxidized Low Density Lipoprotein-Mediated Activation of Phospholipase D in Smooth Muscle Cells: A Possible Role in Cell Proliferation and Atherogenisis*, Natarajan, Scribner, Hart and Parthasarathy, *J. Lipid Res*.
*Thrombotic Mechanisms in Atherosclerosis: Potential Impact of Soy Proteins*, Wilcox and Blumenthal, *J. Nutr.*, vol. 125, Supp. 3, pp. 631s-638s (Mar. 1995).
*Biology of Atherosclerotic Placque Formation: Possible Role of Growth Factors in Lesion Development and the Potential Impact of Soy*, Raines and Ross, *J. Nutr.*, vol. 125, Supp. 3, pp. 624s-630s (Mar. 1995).
*A Soy Protein Isolate Rich in Genistein and Daizden and Its Effects on Plasma Isoflavone Concentrations, Platelet Aggregation, Blood Lipids, and Fatty Acid Composition of Plasma Phospholipid in Normal Men*, Gooderham, Adlercreutz, Ojala, Wahala and Holub, *J. Nutrition*, vol. 126/8, pp. 2000-2006 (1996).
*The Nonhuman Primate Model of the Relationship Between Gonadal Steroids and Coronary Heart Disease*, Clarkson, Hughes and Klein, *Progress in Cardiovascular Diseases*, vol. 38/3, pp. 189-198 (1995).
*Turnover of Very Low-Density Lipoprotein B is Increased by Substitution of Soybean Protein for Meat and Dairy Protein in the Diets of Hypercholesterolemic Men*, Huff et al., *Am. J. of Clin. Nutr.*, vol. 39, pp. 888-897 (Jun. 1984).
*Review of Clinical Studies on Cholesterol-Lowering Response to Soy Protein*, Carroll, *J. Am. Dietetic Assoc.*, vol. 91, No. 7, pp. 820-827 (1991).
*Soybean Protein Diet Increases Low Density Lipoprotein Receptor Activity in Mononuclear Cells From Hypercholesterolemic Patients*, Lovati et al., *J. Clin. Invest.*, vol. 80, pp. 1498-1502 (1987).
*Comparison of Actions of Soy Protein and Casein on Metabolism of Plasma Lipoproteins and Cholesterol in Humans*, Grundy & Abrams, *Am. J. Clin. Nutr.*, vol. 38, pp. 245-252 (Aug. 1983).
*Overview of Proposed Mechanisms for the Hypochoesterolemic Effect of Soy*, Potter, *J. Nutr.*, vol. 125, pp. 606S-611S (1995).
*Isoflavones and Hypercholesterolemia in Rats*, Sharma, *Lipids*, vol. 14, pp. 535-540, (1978).
*Effect of Legume Seeds on Serum Cholesterol*, *Nutrition Reviews*, vol. 38, No. 4, pp. 159-160, (Apr. 1980).
*Effects of Postmenopausal Estrogen Replacement on the Concentrations and Metabolism of Plasma Lipoproteins*; Walsh et al.; *The New England Journal of Medicine*; vol. 325, No. 17, pp. 1196-1204; (Oct. 1991).
*Soy Isoflavones Improve Systemic Arterial Compliance But Not Plasma Lipids in Menopausal and Perimenopausal Women*, Nestel, P. et al., *Arteriosclerosis, Thrombosis and Vascular Biology*, 17(12):3392-3398, (Dec. 1997).
*Dietary Phytosterols: A Review of Metabolism, Benefits and Side Effects*; Ling et al.; *Life Sciences*; vol. 57, No. 3, pp. 195-206; (1995).
*World Oilseeds—Chemistry, Technology, and Utilization*; Salunkhe et al.; *Van Nostrand Reinhold*; pp. 10-13.
*The Analysis of Fats and Oils*; Mehlenbacher; *The Garrard Press*; pp. 589-592.
*High Purified Soybean Protein Is Not Hypocholesterolemic in Rats but Stimulates Cholesterol Synthesis and Excretion and Reduces Polyunsaturated Fatty Acid Biosynthesis*; Madani et al.; *American Society for Nutritional Sciences*; pp. 1084-1091; (1998).
*Plant Sterol-enriched Margarines and Reduction of Plasma Total and LDL-cholesterol Concentrations in Normocholesterolaemic and Mildly Hypercholesterolaemic Subjects*; Weststrate et al.; *European Journal of Clinical Nutrition*; pp. 334-343; 1998).
*Oxidized Low Density Lipoprotein-Mediated Activation of Phospholipase D in Smooth Muscle Cells; A Possible Role in Cell Proliferation and Atherogenisis*, Natarajan, Scribner, Hart and Parthasarathy, *J. Lipid Res*, (Feb. 1997).
*World Oilseeds—Chemistry, Technology, and Utilization*; Salunkhe et al.; *Van Nostrand Reinhold*; pp. 10-13, (Aug. 1992).
*The Analysis of Fats and Oils*; Mehlenbacher; *The Garrard Press*; pp. 589-592, (1955).
*Highly Purified Soybean Protein Is Not Hypocholesterolemic in Rats but Stimulates Cholesterol Synthesis and Excretion and Reduces Polyunsaturated Fatty Acid Biosynthesis*; Madani et al.; *American Society for Nutritional Sciences*; pp. 1084-1091; (1998).

* cited by examiner

β-sitosterol

Campesterol

Stigmasterol

Sitostanol

Campestanol

| Compound | R₁ | R₂ | R₃ | R₄ |
|---|---|---|---|---|
| Genistein | OH | H | OH | OH |
| Daidzein | OH | H | H | OH |
| Glycitein | OH | OCH₃ | H | OH |
| Biochanin A | OH | H | OH | OCH₃ |
| Formononetin | OH | H | H | OCH₃ |

| Compound | R₁ | R₂ | R₃ | R₄ |
|---|---|---|---|---|
| Genistin | H | H | OH | OH |
| 6'-OMal genistin | COCH₂CO₂H | H | OH | OH |
| 6'-OAc genistin | COCH₃ | H | OH | OH |
| Daidzin | H | H | H | OH |
| 6'-OMal daidzin | COCH₂CO₂H | H | H | OH |
| 6'-OAc daidzin | COCH₃ | H | H | OH |
| Glycitin | H | OCH₃ | H | OH |
| 6'-OMal glycitin | COCH₃ | OCH₃ | H | OH |

METHOD OF REDUCING LOW DENSITY LIPROPROTEIN CHOLESTEROL CONCENTRATION

This application is a divisional of patent application Ser. No. 09/826,346 filed Apr. 4, 2001 now U.S. Pat. No. 6,579,534 which is a divisional application of patent application Ser. No. 09/298,528 filed Apr. 23, 1999, now U.S. Pat. No. 6,544,566.

FIELD OF THE INVENTION

The present invention relates to compositions for and methods of reducing low density lipoprotein cholesterol and total cholesterol concentrations in the blood. In particular, the present invention relates to compositions containing plant sterols, soy protein, and isoflavones, and combinations thereof, which are useful for lowering LDL-cholesterol and total cholesterol blood concentrations and for preventing or minimizing development of atherosclerosis.

BACKGROUND OF THE INVENTION

Cardiovascular disease is a leading cause of morbidity and mortality, particularly in the United States and in Western European countries. Several causative factors are implicated in the development of cardiovascular disease including hereditary predisposition to the disease, gender, lifestyle factors such as smoking and diet, age, hypertension, and hyperlipidemia, including hypercholesteremia. Several of these factors, particularly hyperlipidemia and hypercholesteremia, contribute to the development of atherosclerosis, a primary cause of vascular and heart disease.

High blood cholesterol concentration is one of the major risk factors for vascular disease and coronary heart disease in humans. Elevated low density lipoprotein cholesterol (hereafter "LDL-cholesterol") and elevated total cholesterol are directly related to an increased risk of coronary heart disease. *Cholesterol and Mortality: 30 Years of Follow-Up from the Framingham Study*, Anderson, Castelli, & Levy, *JAMA*, Vol 257, pp. 2176-80 (1987).

Ingestion of soy protein materials in the diet is associated with a lower risk of coronary heart disease, which may reflect decreases in serum cholesterol levels. Soy protein materials are known to reduce total cholesterol and LDL-cholesterol levels in the blood of animals. A recent meta-analysis of the effects of soy protein intake on serum lipids in humans has shown that dietary soy protein is significantly related to lowering serum concentrations of total cholesterol and LDL-cholesterol in humans. *Meta-Analysis of the Effects of Soy Protein Intake on Serum Lipids*, Anderson, Johnstone, and Cook-Newell, *N. Engl. J. Med.*, Vol. 333, No. 5, pp. 276-82 (1995).

Ingestion of phytosterols, compounds which are found in whole soybeans, has also been shown to reduce the circulating total and LDL cholesterol levels in the blood. *Dietary Phytosterols: A Review of Metabolism, Benefits, and Side Effects*, Ling & Jones, *Life Sci.*, Vol. 57:3, pp. 195-206 (1995). Phytosterols are sterol compounds produced by plants which are structurally very similar to cholesterol except that they always contain some substitutions at the $C_{24}$ position on the sterol side chain. Common plant sterols include the unsaturated sterols β-sitosterol, campesterol, and stigmasterol, which are shown in FIG. 1, and their saturated counterparts sitostanol and campestanol, shown in FIG. 2. Dietary sources of phytosterols are corn oil, soybean oil, and other plant oils which contain the relatively hydrophobic compounds.

The phytoestrogenic isoflavones, shown in FIGS. 3 and 4, are another set of compounds that are found in whole soybeans which have recently been recognized as a significant factor in reducing LDL and total cholesterol concentrations in the blood. Purified concentrated isoflavones, particularly genistein, suppress the biosynthesis of cholesterol as well as prevent the oxidation of LDL cholesterol, an important step in the development of atherosclerosis. See e.g., Korean Patent No. 97-20103; *Oxidized Low Density Lipoprotein-Mediated Activation of Phospholipase D in Smooth Muscle Cells: a Possible Role in Cell Proliferation and Atherogenesis*, Natarajan et al., *J. Lipid Res.* 36:9 pp. 2005-16 (September 1995).

In the conventional processing of whole soybeans to produce soy oils, soy protein, and pharmaceutical or dietary supplement compositions, the phytosterols, isoflavones, and soy protein are separated. The plant sterols are separated from soy protein and the isoflavones into a soy oil fraction which contains fats and fat solubles by mechanical or chemical extraction of dehulled soybeans, The soy oil fraction is separated from the remaining soy materials—the "defatted soy material"—for use in soy and vegetable oils, which may be further processed to form shortenings, margarines, and lecithin.

The defatted soy materials, usually defatted soy flakes, are used as a starting material to produce products containing substantial amounts of soy protein such as soy protein concentrates and soy protein isolates. The defatted soy materials used to produce soy protein products also contain the isoflavones. However, in conventional processes for the production of soy protein materials such as soy protein concentrates and soy protein isolates, substantial amounts of the isoflavones are separated from the soy protein material by washing the soy protein material with an alcohol extract or an aqueous extract. See, e.g., *Soy Protein Products, Characteristics, Nutritional Aspects, and Utilization*, pp. 3-6 (Pub. Soy Protein Council, 1987).

In the commercial production of soy protein materials the focus has been to separate the isoflavones from the soy protein material since isoflavones have been associated with poor taste, odor, and/or color when present in a soy protein material. For example, U.S. Pat. No. 5,804,234 teaches a process for removing isoflavones from a soybean material by contacting the protein material with an adsorbent resin to produce a better tasting soybean protein. Alcohol extraction of soy protein materials is particularly preferred since alcohol extraction is purported to produce a better tasting vegetable protein material than aqueous extraction, in part because alcohol is quite effective in removing isoflavones from the soy protein material. See, e.g., Japanese Patent No. 63-245,648A.

Recent efforts have also been focused on separating the isoflavones from plant materials in which they occur, particularly soy beans and clover, to provide a purified isoflavone material which can be used to provide health benefits. For example, the following patents disclose various methods of separating isoflavones from plant materials: U.S. Pat. Nos. 4,428,876; 5,702,752; 5,679,806; 4,390,559; 4,366,248; 4,366,082; 4,264,509; 4,232,122; 4,157,984; Japanese Patent Nos. 1-258669A; 5-170756A; 41-90720A; 62-126186A; 62-126185A; and PCT Patent Application No. WO 93/23069. The separated isoflavone compounds may be used in pharmaceutical compositions or dietary supplement compositions to prevent or treat a variety of deleterious health conditions including lowering elevated cholesterol levels. For example, the separated isoflavone materials may be utilized in pharmaceutical or dietary supplement compositions as described in U.S. Pat. Nos. 5,516,528; 5,424,331; 5,569,459; 5,654,011 and PCT Patent Application No. WO 93/23069.

New methods and compositions utilizing soy components and which are capable of providing significant lowering of LDL and total cholesterol levels in the blood to significantly reduce the risk of atherosclerosis and coronary heart disease remain desirable.

SUMMARY OF THE INVENTION

In one aspect, the present invention is a composition containing a soy protein material containing at least 49% soy protein by dry weight of the soy protein material, at least one isoflavone selected from the group consisting of genistein, daidzein, glycitein, biochanin A, formononetein, and their respective naturally occurring glycosides and glycoside conjugates, and a plant sterol, where the plant sterol forms at least 0.49% of the composition by weight.

In another aspect, the present invention is a composition containing a soy protein material which contains at least 49% soy protein by dry weight of the soy protein material, and a plant sterol, where the plant sterol forms at least 0.49% of the composition by weight.

In a further aspect, the present invention is a composition containing at least one isoflavone selected from the group consisting of genistein, daidzein, glycitein, biochanin A, formononetein, and their respective naturally occurring glycosides and glycoside conjugates, and a plant sterol, where the plant sterol forms at least 0.49% of the composition by weight.

In yet another aspect, the present invention is a method for lowering the concentration of LDL and total cholesterol in the blood of a human in which a soy protein material containing at least 49% soy protein by dry weight of the soy protein material, an isoflavone selected from the group consisting of genistein, daidzein, glycitein, biochanin A, formononetein, and their respective naturally occurring glycosides and glycoside conjugates, and a plant sterol are co-administered to the human to decrease the concentration of LDL and total cholesterol in the blood of the human. The plant sterol is co-administered in an amount such that the plant sterol comprises at least 0.49% of the combined weight of the co-administered soy protein material, isoflavone, and plant sterol. In a preferred aspect, the plant sterol, soy protein material, and isoflavone are co-administered to the human to prevent or minimize the development of atherosclerosis in the human.

In still another aspect, the present invention is a method for lowering the concentration of low density lipoprotein cholesterol and total cholesterol in the blood of a human in which a soy protein material containing at least 49% soy protein by dry weight of the soy protein material and a plant sterol are co-administered to a human to decrease the concentration of LDL and total cholesterol in the blood of the human. The plant sterol is co-administered in an amount such that the plant sterol comprises at least 0.49% of the combined weight of the co-administered soy protein material and plant sterol. In a preferred aspect, the plant sterol and the soy protein material are co-administered to the human to prevent or minimize the development of atherosclerosis in the human.

In yet another aspect, the present invention is a method for lowering the concentration of low density lipoprotein cholesterol and total cholesterol in the blood of a human in which a plant sterol and an isoflavone selected from the group consisting of genistein, daidzein, glycitein, biochanin A, formononetein, and their respective naturally occurring glycosides and glycoside conjugates are co-administered to the human to decrease the concentration of LDL and total cholesterol in the blood of the human. The plant sterol is co-administered in an amount such that the plant sterol comprises at least 0.49% of the combined weight of the co-administered isoflavone and the plant sterol. In a preferred aspect, the plant sterol and the isoflavone are co-administered to the human to prevent or minimize the development of atherosclerosis in the human.

In a further aspect, the present invention is a composition containing a soy hypocotyl material and a plant sterol, where the plant sterol forms at least 0.49% of the composition by weight.

DESCRIPTION OF THE PREFERRED EMBODIMENTS

Figure 1:
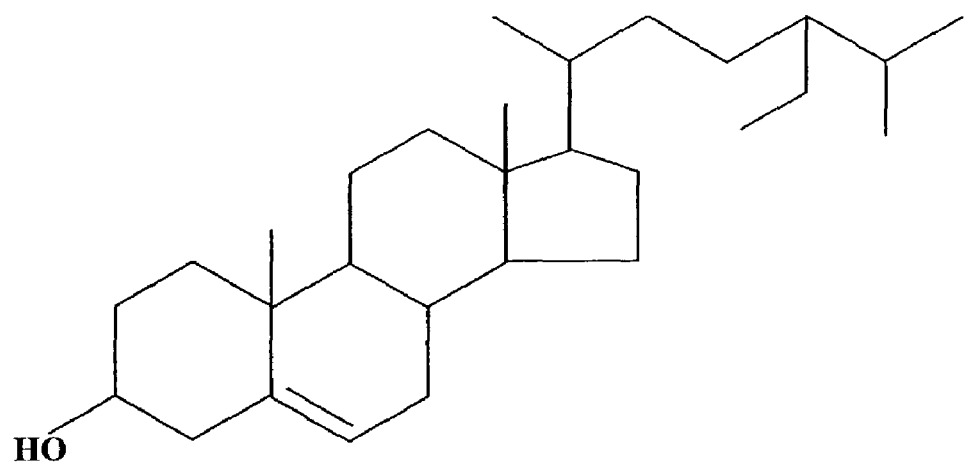
FIG. 1 is a depiction of the molecular structure of the unsaturated plant sterols P-sitosterol, campesterol, and stigmasterol.
Figure 1:
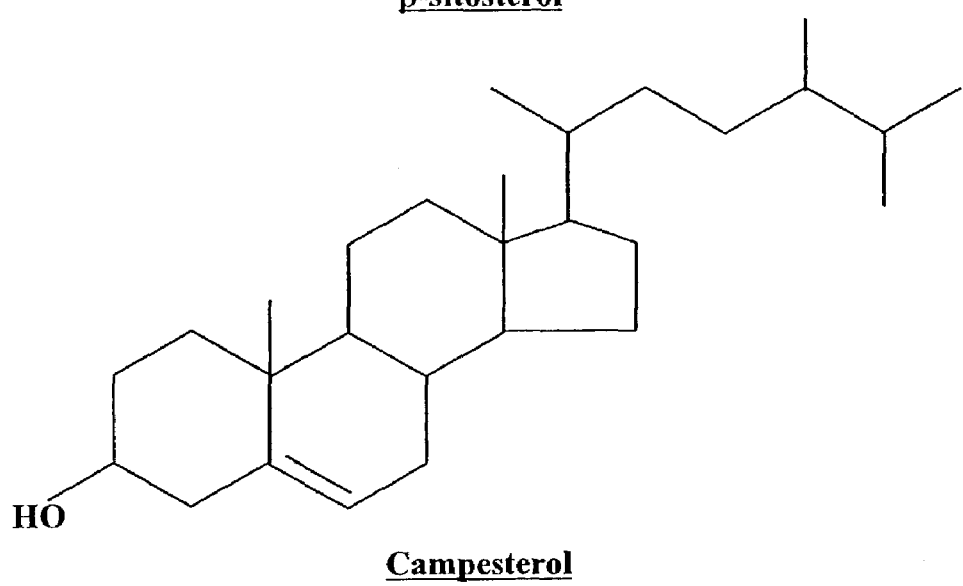
Figure 1:
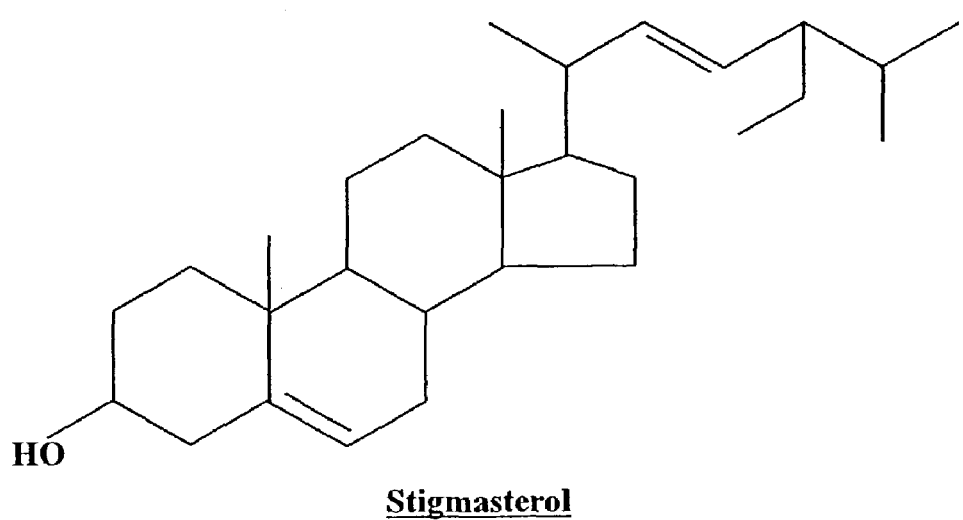

As used herein "Mal" represents "malonyl' and "Ac" represents "acetyl". The term "minimize", or a derivative thereof, includes a complete or partial inhibition of a specified biological effect (which is apparent from the context in which the term minimize is used). Also, as used herein, the term "isoflavone" or "phytoestrogen" may mean both a single isoflavone or phytoestrogen, or plural isoflavones or phytoestrogens when the "isoflavone" or "phytoestrogen" is defined as at least one of a selected group of isoflavones. The term "isoflavone glycoside" refers to an isoflavone moiety having a carbohydrate monomer moiety covalently bonded thereto. The term "isoflavone glycoside conjugate" refers to an isoflavone glycoside having another molecular moiety, such as an ester, bonded to the carbohydrate portion of the isoflavone glycoside. Also, as used herein, a "pharmaceutical preparation" is a compound or a mixture of compounds combined with an excipient which is effective to deliver the compound or compounds to a human as prescribed by a physician. An "over-the-counter preparation" is a compound or mixture of compounds combined with an excipient which is effective to deliver the compound or compounds to a human which does not require a prescription from a physician in order to be administered to the human.

The present invention resides in the discovery that plant sterols in combination with soy protein materials and/or isoflavones synergistically lower low density lipoprotein cholesterol and total cholesterol levels in the blood of a human when co-administered in amounts effective to induce the cholesterol lowering activity of each of the co-administered components. The present invention, therefore, is directed to compositions for and methods of decreasing LDL and total cholesterol concentrations in the blood with combinations of plant sterols (also known as "phytosterols") soy protein materials and/or selected isoflavones. Furthermore, plant sterols in combination with soy protein materials and particularly with isoflavones are effective to prevent or minimize the development of atherosclerosis by reducing the LDL and total cholesterol concentrations in the blood, as well as by antioxidant effects and tyrosine kinase inhibition. Therefore, the present invention is also directed to compositions for and methods of preventing or minimizing the development of atherosclerosis.

Compositions

In one embodiment, the compositions of the present invention include a plant sterol in combination with either a soy protein material containing at least 49% soy protein by dry weight of the soy protein material or with at least one isoflavone selected from genistein, daidzein, glycitein, biochanin A, formononetein, and their naturally occurring glycosides and glycoside conjugates, or a plant sterol in combination with both an isoflavone and a soy protein material. Most preferably the composition contains all three components, a plant sterol, a soy protein material, and an isoflavone, so that the LDL and total cholesterol decreasing effects of each component are cooperatively utilized.

In another embodiment, the compositions of the present invention include a plant sterol in combination with a soy hypocotyl material, which typically contains from about 37% to about 44% soy protein by weight. The soy hypocotyl/plant sterol composition may additionally include at least one isoflavone selected from genistein, daidzein, glycitein, biochanin A, formononetein, and their naturally occurring glycosides and glycoside conjugates.

Plant Sterols

Figure 2:
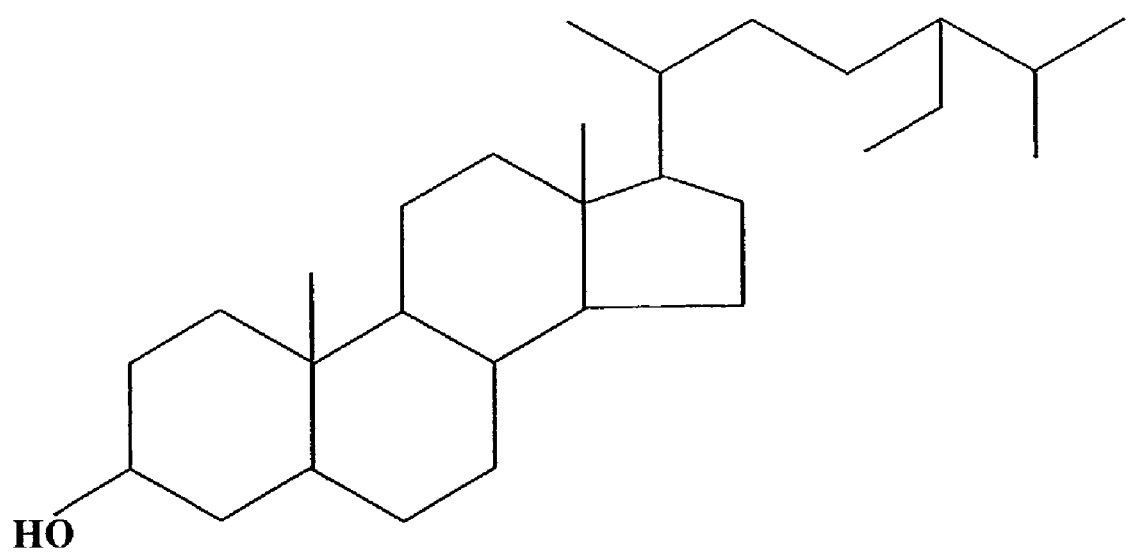
FIG. 2 is a depiction of the molecular structure of the saturated plant sterols sitostanol and campestanol.
Figure 2:
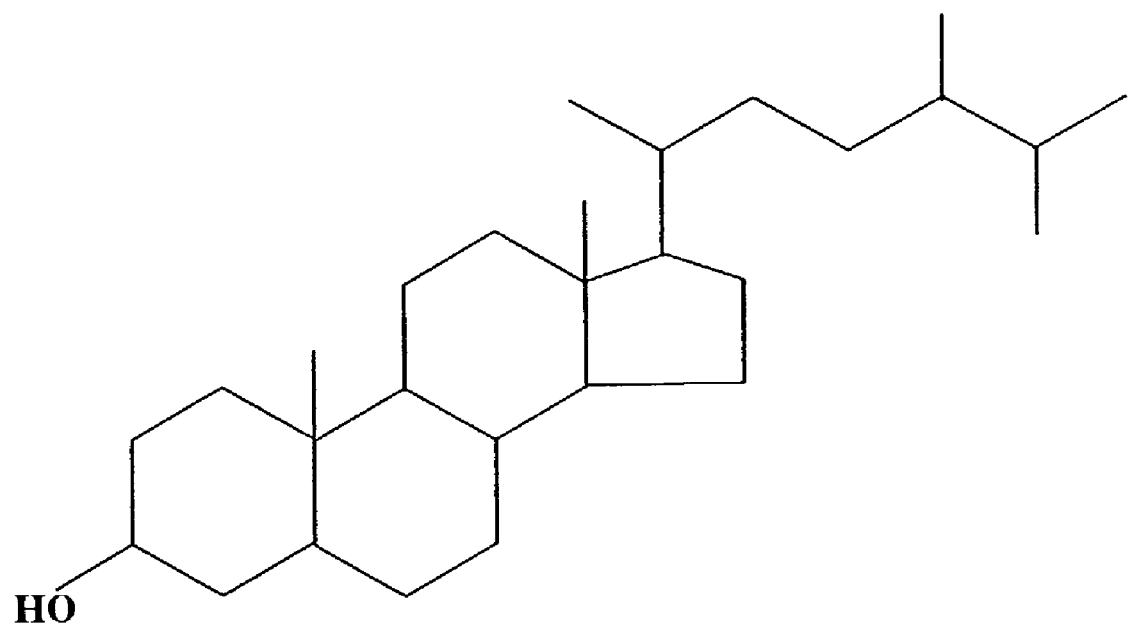

The plant sterols which may be used in the composition include both saturated and unsaturated plant sterols. Preferred unsaturated plant sterols which may be utilized in the composition of the invention are β-sitosterol, campesterol, and stigmasterol, shown in FIG. 1, and preferred saturated plant sterols which may be used in the composition are campestanol and sitostanol, shown in FIG. 2. The unsaturated sterols β-sitosterol and campesterol are particularly preferred.

The amount of plant sterols in the present composition is at least 0.49% of the total weight of the composition, more preferably from about 0.5% to about 99.5% of the total weight of the composition, and most preferably from about 1% to about 60% of the total weight of the composition. The relative amount of plant sterols in the composition will depend on whether the composition contains a soy protein material. If the composition contains a soy protein material, generally the amount of plant sterols in the composition, as a percent of the total weight of the composition, will be significantly less than if the composition does not contain a soy protein material.

Soy Protein Materials

In one embodiment, the soy protein materials which may be used in a composition of the present invention are soy protein materials which contain at least 49% soy protein by dry weight of the soy protein containing material. Preferred soy protein materials which contain at least 49% soy protein by dry weight are defatted soy flours and soy flakes, which contain from 49% soy protein to about 65% soy protein by weight; soy protein concentrates, which contain from at least 65% soy protein to about 90% soy protein by weight; and soy protein isolates, which contain at least 90% soy protein by weight. Soy protein concentrates and soy protein isolates are particularly preferred. In another embodiment, the soy protein materials that may be used in a composition of the present invention are soy hypocotyl materials.

The amount of soy protein materials in the present composition ranges from 0% to 99.55% by total weight of the composition. When a soy protein material is included in the composition, it preferably comprises at least a majority of the composition, more preferably being present from about 55% to about 99.55%, even more preferably from about 75% to about 99.55%, and most preferably from about 80% to about 99.5% of the total weight of the composition. A soy protein material will be always be included in the composition if the composition contains no isoflavones.

Isoflavones

Figure 3:
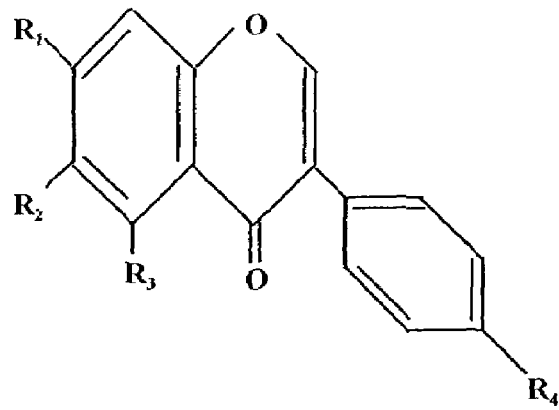
FIG. 3 is a depiction of the molecular structure of the aglucone isoflavones utilized in the invention.
Figure 4:
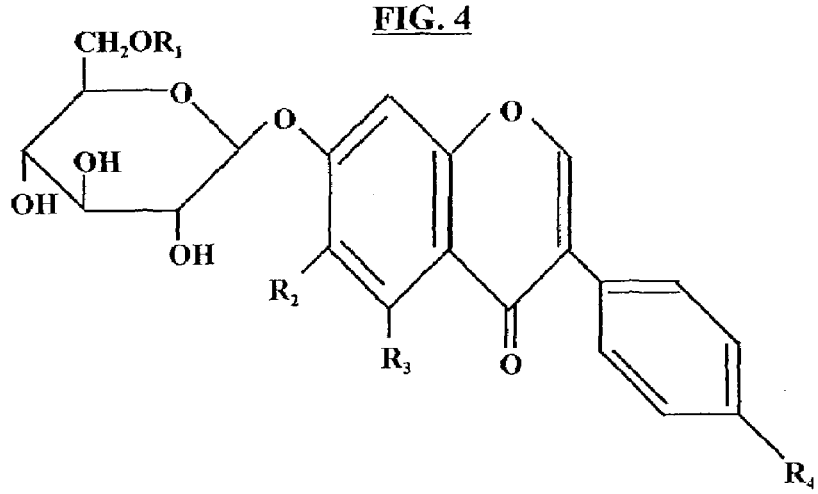
FIG. 4 is a depiction of the molecular structure of representative isoflavone glycosides and isoflavone glycoside conjugates.

The isoflavones which may be used in a composition of the present invention are the aglucone isoflavones genistein, daidzein, glycitein, biochanin A, formononetein, shown in FIG. 3, and the naturally occurring glycosides and glycoside conjugates of these aglucone isoflavones including genistin, 6"-O-Mal genistin, 6"-O-Ac genistin, daidzin, 6"-O-Mal daidzin, 6"-O-Ac daidzin, glycitin, and 6"-O-Mal glycitin, shown in FIG. 4. One or more of the isoflavones may be used in the composition. The aglucone isoflavones are particularly preferred since they are the most biologically active of the isoflavones. The most preferred isoflavones for use in the composition are genistein, daidzein, biochanin A and/or formononetein.

The amount of isoflavone in the composition ranges from 0% to about 66%, by total weight of the composition When the soy protein material is included in the composition the amount of isoflavone in the composition ranges from about 0% to about 15% by total weight of the composition. Most preferably the isoflavone is present in an amount from about 0.0066% to about 10% of the composition by total weight. The isoflavone will always be included in the composition if the composition contains no soy protein material.

The composition of the present invention may be prepared by obtaining and combining the above described components using processes and procedures well known in the art.

The plant sterol may be obtained by extracting and isolating a plant sterol from a plant or by chemically synthesizing the sterol. Alternatively, an oil containing a plant sterol which is extracted from a plant containing plant sterols may be utilized in the composition in sufficient amounts to provide the desired levels of plant sterol in the composition, where the oil is extracted from the plant in accordance with conventional methods for recovering plant oils.

In a preferred embodiment the plant sterol is obtained from soy oil as a nonsaponifiable fraction of the soy oil according to the method provided in U.S. Pat. No. 3,993,756 (particularly Example 10), which is incorporated herein by reference. Briefly, a nonsaponifiable fraction of soybean oil containing about 40-50% by weight plant sterols is obtained from whole soybeans. Soy oil is obtained from the whole soybeans by conventional cracking, dehulling, flaking, and extraction procedures. The soy oil is purified by conventional soy oil purification procedures until the final deodorization step. The deodorization of the soy oil is conducted at 225° C.-235° C. at reduced pressures of 2-3 mm Hg to distill and separate an extract containing the plant sterols from the soy oil. The free fatty acids contained in the extract are converted to methyl esters by refluxing the extract with methanol and concentrated sulfuric acid. (by weight 1 g extract: 1.72 g methanol:0.019 g sulfuric acid) at 65-70° C. for 3-4 hours. After stopping the reaction, the methanol is removed under reduced pressure and the residual oily material is washed with water at 80°-100° C. to remove the sulfuric acid. The methyl esters of the fatty acids are then removed by distillation at 170-190° C. at 20-30 mm Hg. The resulting residue is purified to provide a nonsaponifiable fraction of soybean oil containing 40-50% plant sterols. The plant sterols in the nonsaponifiable fraction are β-sitosterol, campesterol, and stigmasterol. The non-saponifiable fraction may be further purified by HPLC to obtain each individual plant sterol, or more preferably, may be used directly as the plant sterol source in the present composition.

β-sitosterol may also be extracted from several other plant oils according to known procedures. β-sitosterol can be isolated from wheat germ oil and from corn oil according to the procedures set forth by Anderson et al in *J. Am. Chem. Soc.*, 48, 2897 (1926); from rye germ oil by the method of Gloyer et al in *J. Am. Chem. Soc.*, 61, 1901 (1939); from cottonseed oil by the method of Wallis in *J. Org. Chem.*, 2, 335 (1937); and from tall oil by the method of Sandqvist et al in *Ber.* 64, 2167 (1931), all incorporated herein by reference.

Campesterol may be extracted from other plant oils as well according to known procedures provided by Fernholz et al in *J. Am. Chem. Soc.*, 63, 1155 (1941), which is incorporated herein by reference. Campesterol may also be synthesized by the procedure of Tarzia et al, *Gazz. Chim. Ital*, 97, 102 (1967) and *Chem Abstr.*, 67, 32883q (1967), which are incorporated herein by reference. Stigmasterol may be isolated from soy or calabar beans.

The saturated plant sterols may be obtained from their unsaturated counterparts by hydrogenation. Utilizing conventional hydrogenation procedures β-sitosterol and stigmasterol may be converted to sitostanol and campesterol may be converted to campestanol.

Certain of the plant sterols are commercially available, and may purchased directly for incorporation into the present composition. For example, campesterol and stigmasterol may be purchased from Aldrich Chemical Company, Inc., 940 West Saint Paul Avenue, Milwaukee, Wis. β-sitosterol and sitostanol may be purchased from Sigma Chemical Company, 3050 Spruce Street, St. Louis, Mo.

In one embodiment, the soy protein material is a defatted soy protein flour or grit, a soy protein concentrate, or a soy protein isolate, each of which contains at least 49% soy protein by weight. To obtain a defatted soy flour or soy grit, whole soybeans are cleaned, cracked, flaked, and defatted according to conventional soybean processing methods to produce defatted soy flakes, chips, meal, or cake, from which soy flour and soy grit may be produced. Defatted soy flakes and soy meal are also commercially available. Defatted soy flour and defatted soy grit are produced from the defatted soy flakes, chips, meal, or cake by comminuting the material into a finely divided form according to conventional processes. The defatted soy flour is comminuted into particles sized 150μ or less (sufficient to permit the particles to pass through a No. 100 U.S. screen mesh), and the defatted soy grit is comminuted into particles sized from about 150μ to about 2000μ (sufficient to permit the particles to pass through No. 10-No. 80 U.S. screen meshes). The defatted soy flour and the defatted soy grit contain from 49% soy protein to about 65% soy protein by weight, where the remainder of the soy flour and soy grit is formed of primarily of carbohydrates, soy fiber, and ash. Defatted soy flour and soy grit are commercially available and may be acquired for direct incorporation into the present composition.

Preferably the soy protein material used in the composition is a soy protein concentrate or a soy protein isolate, which contain significantly more soy protein than a soy flour or grit. A soy protein concentrate contains from about 65% soy protein to about 90% soy protein by weight, where the remainder of the soy protein concentrate is primarily soy fiber and other polysaccharides. A soy protein concentrate for use in the composition of the present invention may be formed by conventional processes for producing soy protein concentrates which include (i) washing defatted soy flakes or soy flour with an aqueous alcohol, preferably aqueous ethanol or methanol; (ii) washing defatted soy flakes or soy flour with a dilute acid having a pH at about the isoelectric point of soy protein (pH 4.4-4.6); or (iii) heating defatted soy flakes or soy flour with moisture to denature the protein, then washing the flakes or flour with water. Soy protein concentrates are commercially available and may be acquired for direct incorporation into the present compositions.

Most preferably the soy protein material used in the composition of the invention is a soy protein isolate (also known as an isolated soy protein), which has the highest soy protein content of processed soy protein materials. A soy protein isolate contains at least about 90% soy protein by weight, where the remainder of the soy protein isolate is primarily formed of ash and moisture. A soy protein isolate for use in the composition of the present invention may be formed by a conventional process for forming soy protein isolates in which defatted soy flakes are extracted with an aqueous solution having a pH of from about 6 to about 11, preferably a dilute aqueous sodium, calcium, or ammonium hydroxide solution, and an extract containing soluble protein is separated from insoluble materials such soy fiber and other insoluble polysaccharides. The pH of the separated extract is adjusted to about the isoelectric point of soy protein, preferably about pH 4.4-4.6, to precipitate the protein. The precipitated protein is separated from the liquid fraction of the extract to separate the protein from soluble carbohydrates. The separated protein is then washed, and may be neutralized, to provide the soy protein isolate. Soy protein isolates are commercially available and may be acquired for direct incorporation into the composition of the present invention.

In another embodiment, the soy protein material is a soy hypocotyl material, which contains from about 37% to about 44% soy protein by weight. To obtain a soy hypocotyl material, whole soybeans are dehulled, and the soy cotyledons are split in accordance with conventional soy processing techniques. The hypocotyls become separated following the splitting of the cotyledons, and may be separated and isolated by passing the disturbed soybeans over a sieve of sufficient pore size to selectively remove the small hypocotyl. The raw hypocotyl may be ground or milled to produce a powder or flour.

The isoflavone compounds utilized in the present compositions are naturally occurring substances which may be found in plants such as legumes, clover, and the root of the kudzu vine (pueraria root). Common legume sources of these isoflavone compounds include soy beans, chick peas, and various other types of beans and peas. Clover sources of these isoflavone compounds include red clover and subterranean clover. Soy beans are a particularly preferred source of the isoflavone compounds (except biochanin A and its glycosides which are not present in soy).

The isoflavone compounds may be obtained from the plant sources in which they naturally occur, and several of the isoflavone compounds may be synthetically prepared by processes known in the art. For example, daidzein may be isolated from red clover as disclosed by Wong (*J. Sci. Food Agr.*, Vol. 13, p. 304 (1962)) or may be isolated from the mold *Micromonospora halophytica* as provided by Ganguly and Sarre (*Chem. & Ind.* (*London*), p. 201 (1970)), both references of which are incorporated by reference herein. Daidzein may be synthetically prepared by the methods provided by Baker et al (*J. Chem. Soc.*, p. 274 (1933)), Wesley et al. (*Ber.* Vol. 66, p. 685 (1933)), Mahal et al. (*J.*

*Chem. Soc.*, p. 1769 (1934)), Baker et al. (*J. Chem. Soc.*, p. 1852 (1953)), or Farkas (*Ber.* Vol. 90, p. 2940 (1957)), each reference of which is incorporated herein by reference. The isoflavone glycoside daidzin may be synthetically prepared by the method of Farkas et al. (*Ber.*, Vol. 92, p. 819 (1959)), incorporated herein by reference. The daidzein isoflavone glycoside conjugates 6'-O-Mal daidzin and 6'-O-Ac daidzin can be prepared by a conventional saponification of daidzin with a malonyl or an acetyl anhydride, respectively.

Genistein may be synthetically prepared by the methods provided by Baker et al (*J. Chem. Soc.*, p. 3115 (1928)); Narasimhachari et al. (*J. Sci. Ind. Res.*, Vol. 12, p. 287 (1953)); Yoder et al., (*Proc. Iowa Acad. Sci.*, Vol. 61, p. 271 (1954); and Zemplen et al. (*Acta. Chim. Acad. Sci. Hung.*, Vol. 19, p. 277 (1959)), each reference of which is incorporated herein by reference. The isoflavone glycoside genistin may be synthetically prepared by the method of Zemplen et al. (*Ber.*, Vol 76B, p. 1110 (1943)), incorporated herein by reference. The isoflavone conjugates of genistin, 6'-O-Mal genistin and 6'-O-Ac genistin, can be prepared by a conventional saponification of genistin with a malonyl or an acetyl anhydride, respectively.

Biochanin A can be synthetically prepared by the method provided by Baker et al. (*Nature* 169:706 (1952)), incorporated herein by reference. Biochanin A can also be separated from red clover by the method provided by Pope et al. (*Chem. & Ind.* (*London*) p. 1092 (1953)), incorporated herein by reference. Formononetein can be synthetically prepared by the methods disclosed by Wessely et al. (*Ber.* 66:685 (1933)) and Kagel et al. (*Tetrahedron Letters*, p. 593 (1962)), both references of which are incorporated herein by reference. Formononetein can be isolated from soybean meal by the method of Walz (*Ann.* 489:118 (1931)) or can be isolated from clover species by the method of Bradbury et al. (*J. Chem. Soc.* p. 3447 (1951)), both references of which are incorporated herein by reference.

In a most preferred embodiment, the isoflavone component of the present composition is recovered in a soy protein material which is also utilized in the composition. As noted above, isoflavones are naturally occurring compounds in soy. In the production of soy protein flours, grits, concentrates, and isolates some of the isoflavones may be retained in the soy protein materials. Utilization of appropriate processing techniques while processing the soy protein material as described above to produce soy protein flours, grits, concentrates, or isolates will increase the amount of isoflavones retained in the soy protein materials significantly over conventionally processed soy protein materials. Particularly, alcohol washing or extraction of the soy protein material should be avoided since isoflavones are highly soluble in aqueous alcohol, and soy protein concentrates should not be produced by alcohol washing if isoflavones are to be retained in the soy protein material. Furthermore, aqueous washing of the soy protein material should be minimized since washing removes the isoflavones from the soy protein. Washing, if conducted, should be conducted at cool to cold temperatures (from 0° C. to 45° C.) to maximize the insolubility of the isoflavones in the water wash and minimize the loss of isoflavones in the wash. The isoflavones in the soy protein material should be converted to their aglucone form, as described below, to minimize solubility in water prior to washing or extracting the soy protein material with water. Use of the above measures aids in the retention of the isoflavones in the soy protein material soy that the resulting soy protein material contains significant amounts of isoflavones.

In another embodiment, the isoflavone or isoflavones are separated from plant materials in which they naturally occur for use in the present compositions. A preferred method of isolating the isoflavone compounds from plant materials in which they naturally occur is to extract the plant materials with an alcohol, preferably methanol or ethanol, or an aqueous solution, preferably an aqueous alkaline solution, to remove the isoflavones from the plant material. It is preferred to comminute the plant material before extracting the isoflavone compounds to maximize recovery of the isoflavone compounds from the plant material. The isoflavone compounds can be isolated from the extract by conventional separation procedures such as reverse phase high performance liquid chromatography ("HPLC").

In a preferred embodiment, the isoflavone compounds genistein, genistin, 6'-O-Mal genistin, 6'-O-Ac genistin, daidzein, daidzin, 6'-O-Mal daidzin, 6'-O-Ac daidzin, glycitein, glycitin, and 6'-O-Mal glycitin are isolated from a soy material, preferably a commercially available soy material. Soy materials from which the isoflavone compounds can be isolated include: soy beans, dehulled soy beans, soy meal, soy flour, soy grits, soy flakes (full fat and defatted), soy cotyledons, soy hypocotyls, soy molasses, soy protein concentrate, soy whey, soy whey protein, and soy protein isolate. In one embodiment, the isoflavones are extracted from soy beans, dehulled soy beans, soy meal, soy flour, soy grits, soy flakes, soy protein concentrate, soy whey protein, or soy protein isolate, preferably soy meal, soy flour, soy grits, or soy flakes, with a low molecular weight organic extractant, preferably an alcohol, ethyl acetate, acetone, or ether, and most preferably aqueous ethyl alcohol or methyl alcohol. Most preferably the extractant has a pH of about the isoelectric point of soy protein (about pH 4 to pH 5) to minimize the amount of soy protein extracted by the extractant.

The extractant containing the isoflavones is separated from the insoluble soy materials to form an isoflavone enriched extract. If desired, an isoflavone enriched material may be recovered by concentrating the extract to remove the solvent, thereby producing a solid isoflavone enriched material which may be utilized in the compositions and methods of the present invention.

In a more preferred embodiment the isoflavone compounds are further purified from other soy materials soluble in the extract. The isoflavone containing extract is contacted with a material which adsorbs the isoflavones in the extract, and the adsorbed isoflavones are eluted out of the adsorbent material with a solvent which causes the isoflavones to be differentially eluted from the adsorbent material.

In a preferred embodiment, the isoflavones are separated from impurities in the extract by a conventional reverse phase HPLC separation. After extraction of the isoflavones from the soy material and separation of the extract from the insoluble soy materials, the extract is filtered to remove insoluble materials that could plug an HPLC column. An HPLC column is prepared by packing a conventional commercially available HPLC column with a particulate adsorbent material which will releasably bind the isoflavones and impurities in the extract in a compound specific manner. The adsorbent material may be any reverse phase HPLC packing material, however, a preferred packing material may be chosen by the criteria of load capacity, separation effectiveness, and cost. One such preferred packing material is Kromasil C18 16 μm 100 Å beads available from Eka Nobel, Nobel Industries, Sweden.

The filtered extract is passed through the packed HPLC column until all the binding sites of the column are fully saturated with isoflavones, which is detected by the appearance of isoflavones in the effluent from the column. The HPLC column may then be eluted with a solvent to effect the separation. In a preferred embodiment, the eluent is a polar solvent such as ethanol, methanol, ethyl acetate, or acetonitrile, and preferably is an aqueous alcohol having an alcohol content of between about 30% and about 90%, most preferably about 50%, and most preferably the alcohol is ethanol.

The isoflavone compounds and impurities are separately collected from the column effluent. The isoflavone fractions of the eluent may be identified from other eluent fractions in accordance with conventional HPLC and analytical chemistry techniques. The isoflavone fractions of the eluent may be collected from the column, and the volatile content of the solvent (e.g. alcohol) can be removed by evaporation. The isoflavone compounds can be recovered directly if the all of the solvent is removed by evaporation, or may be recovered by chilling the remaining solvent (e.g. water) and centrifuging or filtering the isoflavones from the remaining solvent.

In a particularly preferred embodiment isoflavone glycoside conjugates and isoflavone glycosides recovered from a plant material are converted to their respective aglucone isoflavone forms. The conversion of the isoflavone glycoside conjugates and isoflavone glycosides to the aglucone isoflavones can be effected in the substrate from which the phytoestrogenic isoflavones are to be extracted prior to the extraction, or may be effected in the isoflavone enriched extract after separation of the extract from the insoluble plant materials. The aglucone isoflavone compounds are believed to be particularly active in decreasing LDL and total blood cholesterol concentrations and in preventing or minimizing the development of atherosclerosis. The aglucone isoflavones are also more easily separated from an extract containing water than their respective glycoside conjugate and glycoside forms since the aglucones are less water soluble.

The isoflavone glycoside conjugates (e.g. 6"-O-Mal genistin, 6"-O-Ac genistin, 6"-O-Mal daidzin, 6"-O-Ac daidzin, and 6"-O-Mal glycitin) can be converted to their respective glycosides (e.g. genistin, daidzin, and glycitin) by forming an aqueous alkaline solution of an extract or substrate containing the isoflavones having a pH of about 6 to about 13, preferably about pH 9 to about pH 11, and treating the aqueous alkaline solution at a temperature of about 2° C. to about 121° C., preferably about 25° C. to about 75° C., for a period of time sufficient to effect the conversion, preferably about 30 minutes to about 5 hours, more preferably about 30 minutes to about 1.5 hours. The isoflavone glycosides (e.g. genistin, daidzin, and glycitin) can be converted to their respective aglucone forms (e.g. genistein, daidzein, and glycitein) by contacting the isoflavone glycosides with an enzyme capable of cleaving a 1,4-β-glycoside bond—preferably a commercially available beta-glucosidase enzyme, an alpha- or beta-galactosidase enzyme, a pectinase enzyme, a lactase enzyme, or a gluco-amylase enzyme—at a pH at which the enzyme is active, typically from about pH 3 to about pH 9, and at a temperature of about 25° C. to about 75° C., more preferably about 45° C. to about 65° C., for a period of time sufficient to effect the conversion, typically about 1 hour to about 24 hours, preferably about 1 hour to about 3 hours.

The aglucone isoflavones can be separated from a plant substrate using conventional separation procedures. For example, the aglucone isoflavones may be extracted from a soy or clover substrate with a low molecular weight alcohol. The aglucone isoflavones may be separated from the extract by conventional recrystallization processes, or by HPLC. In a particularly preferred embodiment, an isoflavone composition isolated from a soy substrate and utilized in the present compositions or methods includes at least 40% genistein, at least 15% daidzein, and at least 1% glycitein. In another particularly preferred embodiment of the invention, an isoflavone composition isolated from a soy substrate and utilized in the present compositions or methods contains at least 85% genistein, at least 5% daidzein, and at least 0.5% glycitein.

Several of the isoflavone compounds utilized in the present composition are commercially available, and may be purchased for formulation into the present compositions or used in the present methods of the invention. For example, genistein, daidzein, and glycitein are commercially available and may be purchased from Indofine Chemical Company Inc., P.O. Box 473, Somerville, N.J. 08876. Biochanin A is available from Aldrich Chemical Company, Inc., 940 West Saint Paul Avenue, Milwaukee, Wis. 53233.

The plant sterol and the soy protein material and/or the isoflavone may be combined into a composition of the present invention by adding the components together, and preferably thoroughly mixing them. For example, the plant sterol and the soy protein material and/or the isoflavone may be combined by placing the materials in a chopping or a mixing bowl and mixing the materials for a sufficient time to thoroughly blend them.

Preferably the components are mixed together so that the resulting composition contains a biologically active amount of each of the components, although the composition is not limited to having biologically active amounts of each component therein since the composition may be administered more than once in order to achieve a desired decrease in LDL and total cholesterol blood concentrations. Preferably the composition contains from about 500 mg to about 50 g of plant sterols therein, and more preferably from about 1 g to about 10 g of the plant sterols. When the composition contains a soy protein material preferably from about 5 g to about 100 g of the soy protein material is present in the composition, and more preferably from about 10 g to about 40 g of the soy protein material is present in the composition. When the composition contains isoflavones preferably from about 10 mg to about 1000 mg of the isoflavones are present in the composition, and more preferably from about 25 mg to about 200 mg of the isoflavones are present in the composition.

In a preferred embodiment the plant sterol and the soy protein material and/or the isoflavone are formulated into a pharmaceutical or over-the-counter delivery system with suitable excipients. Pharmaceutical or over-the-counter formulations incorporating the plant sterol and the soy protein material and/or the isoflavone can be prepared by procedures known in the art. For example, the components of the present invention can be formulated into tablets, capsules, powders, suspensions, solutions for parenteral administration including intravenous, intramuscular, and subcutaneous administration, and into solutions for application onto patches for transdermal application with common and conventional carriers, binders, diluents, and excipients.

Inert pharmaceutically acceptable excipients useful to form pharmaceutical or over-the-counter formulations in accordance with the present invention include starch, mannitol, calcium sulfate, dicalcium phosphate, magnesium stearate, silicic derivatives, and/or sugars such as sucrose, lactose, and glucose. Binding agents include carboxymethyl cellulose and other cellulose derivatives, gelatin, natural and synthetic gums including alginates such as sodium alginate, polyethylene glycol, waxes and the like. Diluents useful in the invention include a suitable oil, saline, sugar solutions such as aqueous dextrose or aqueous glucose, and glycols such as polyethylene or polypropylene glycol. Other excipients include lubricants such as sodium oleate, sodium acetate, sodium stearate, sodium chloride, sodium benzoate, talc, and magnesium stearate, and the like; disintegrating agents including agar, calcium carbonate, sodium bicarbonate, starch, xanthan gum, and the like; and adsorptive carriers such as bentonite and kaolin. Coloring and flavoring agents may also be added to the pharmaceutical or over-the counter formulations.

In another preferred embodiment dietary supplements incorporating the plant sterol and the soy protein material and/or the isoflavone can be prepared by adding each of the components to a food as a food ingredient, or by adding a mixture of the components to a food as a food ingredient. The foods to which these components may be added include almost all foods, but most preferably are foods in which soy protein materials or vegetable oils containing plant sterols are used as functional ingredients. For example, the plant sterol and the soy protein material and/or the isoflavone can be added to foods including, but not limited to, meats such as ground meats, emulsified meats, and marinated meats; beverages such as nutritional beverages, sports beverages, protein fortified beverages, juices, milk, milk alternatives, and weight loss beverages; cheeses such as hard and soft cheeses, cream cheese, and cottage cheese; frozen desserts such as ice cream, ice milk, low fat frozen desserts, and non-dairy frozen desserts; yogurts; soups; puddings; bakery products; salad dressings; and dips and spreads such as mayonnaise and chip dips. Most preferably the plant sterol and the soy protein material, with or without the isoflavones, are mixed in a aqueous slurry to form an emulsion which is particularly useful in emulsive foods and beverages such as salad dressings, yogurts, soy cheeses, emulsified meats, and powdered beverages.

The following non-limiting formulations illustrate pharmaceutical and dietary formulations including the plant sterols and the soy protein and/or the isoflavone compounds in accordance with the compositions of the present invention and which may be used in accordance with the methods of the present invention.

FORMULATIONS

The following Formulations 1-4 illustrate pharmaceutical or over-the-counter formulations including a plant sterol and a soy protein material and/or an isoflavone useful in the compositions of the present invention.

Formulation 1
 Gelatin Capsules
 Hard gelatin capsules are prepared using the following ingredients: Isoflavone 25-100 mg/capsule; Plant sterol 500-2000 mg/capsule; Starch, NF 0-1000 mg/capsule; Starch flowable powder 0-1000 mg/capsule; Silicone fluid 350 centistokes 0-20 mg/capsule. The ingredients are mixed, passed through a sieve, and filled into capsules.

Formulation 2
 Tablets
 Tablets are prepared using the following ingredients: Plant sterol 250-500 mg/tablet; Soy protein material 1000-2000 mg/tablet; Microcrystalline cellulose 20-300 mg/tablet; Starch 0-50 mg/tablet; Magnesium stearate or stearate acid 0-15 mg/tablet; Silicon dioxide, fumed 0-400 mg/tablet; silicon dioxide, colloidal 0-1 mg/tablet, and lactose 0-100 mg/tablet. The ingredients are blended and compressed to form tablets.

Formulation 3
 Suspensions
 Suspensions are prepared using the following ingredients: Isoflavone 0.1-200 mg/5 ml; Plant sterol 250-2000 mg/5 ml; Soy protein material 500-2000 mg/5 ml; Sodium carboxymethyl cellulose 50-700 mg/5 ml; Sodium benzoate 0-10 mg/5 ml; Purified water 5 ml; and flavor and color agents as needed.

Formulation 4
 Parenteral Solutions
 A parenteral composition is prepared by stirring 1.5% by weight of active ingredients (active ingredients being soy protein material, plant sterol, and isoflavone in a weight ratio of 5:4:1) in 10% by volume propylene glycol and water. The solution is made isotonic with sodium chloride and sterilized.

The following Formulations 5-8 illustrate dietary supplements that may be formed using a plant sterol and a soy protein isolate rich in the isoflavone compounds utilized in the present compositions. The isoflavone rich soy protein isolate in the following examples typically contains between about 1 to about 7 milligrams of the isoflavone compounds per gram of soy protein.

Formulation 5
 Ready to Drink Beverage
 A ready to drink beverage is formed of the following components:

| Ingredient | Percent of composition, by weight |
| --- | --- |
| Water | 75-82 |
| Isoflavone rich soy protein isolate | 10-15 |
| Plant sterol | 3-5 |
| Sucrose | 5-8 |
| Cocoa | 0.1-1 |
| Vitamins/Minerals | 0.1-1 |
| Flavor | 0.1-1 |
| Cellulose gel | 0.1-0.5 |

The ready to drink beverage may be served in 8 ounce servings containing about 20 grams of isolated soy protein including about 20 to about 140 milligrams of the isoflavone compounds and about 6 grams of plant sterol.

Formulation 6
 Powdered Beverage
 A powdered beverage is formed of the following components:

| Ingredient | Percent of composition, by weight |
| --- | --- |
| Isoflavone rich soy protein isolate | 75-85 |
| Plant sterol | 5-10 |
| Sucrose | 8-15 |
| Maltodextrin | 1-5 |
| Vitamins/Minerals | 0.5-2 |
| Aspartame | 0-0.5 |
| Flavor | 0-0.5 |

30 grams of the powdered beverage formulation may be added to water to form a serving containing about 23 grams of soy protein isolate including about 23 to about 161 milligrams of the isoflavone compounds and about 2.5 grams of plant sterol.

Formulation 7
  Food Bar
  A food bar is formed of the following components:

| Ingredients | Percent of composition, by weight |
| --- | --- |
| Isoflavone rich soy protein isolate | 20-30 |
| Plant sterol | 1-5 |
| Corn syrup | 30-45 |
| Rice syrup solids | 7-14 |
| Glycerin | 1-5 |
| Cocoa | 2-7 |
| Compound coating | 15-25 |

The food bar may be served in 70 gram portions containing about 15 grams of soy protein isolate having about 15 to about 105 milligrams of the isoflavone compounds and about 2 grams of plant sterol.

Formulation 8
  Soy Yogurt
  A soy yogurt is formed of the following components:

| Ingredients | Percent of composition, by weight |
| --- | --- |
| Water | 50-70 |
| Isoflavone rich soy protein isolate | 5-15 |
| Plant sterol | 5-15 |
| Sucrose | 3-8 |
| Corn starch | 1-5 |
| Dextrin | 0.3-1 |
| Cellulose gel | 1-3 |
| Culture (yogurt) | 0.01-0.1 |
| Fruit | 10-20 |
| Vitamins/Minerals | 0.05-0.3 |

The soy yogurt may be served in a 170 grain serving containing about 17 grams of soy protein isolate having about 17 to about 170 milligrams of isoflavone compounds and containing about 17 grams of plant sterol.

Methods

The present invention is also directed to methods of decreasing the blood concentration of low density lipoprotein cholesterol or total cholesterol in a human with a plant sterol and a soy protein material and/or an isoflavone compound. To decrease the blood concentration of LDL cholesterol and total cholesterol the plant sterol is co-administered to the human with the soy protein material and/or the isoflavone compound on an ongoing regular basis, preferably daily. The plant sterol is preferably β-sitosterol, campesterol, stigmasterol, sitostanol or campestanol, as described above. The soy protein material is either a soy hypocotyl material or a soy protein material containing at least 49% soy protein by dry weight of the soy protein material such as a soy flour, grit, concentrate, or isolate. The isoflavone compound is selected from one or more of genistein, daidzein, glycitein, biochanin A, formononetin, and their naturally occurring glycosides or glycoside conjugates, as described above. The plant sterol and the soy protein material and/or the isoflavone are preferably administered in a pharmaceutical or over-the-counter composition or as a dietary supplement, as described above, depending on which route is more effective and/or acceptable.

The plant sterol and the soy protein material and/or the isoflavone compound may be co-administered either concurrently or sequentially within a specified period of time, preferably daily, on a periodic basis. Most preferably the plant sterol and the soy protein material and/or the isoflavone compound are co-administered concurrently in a composition of the present invention, described above. Alternatively, the plant sterol and the soy protein and/or the isoflavone compound are administered sequentially as separate components. "Sequentially" as used herein is intended to mean administration of each component individually within a specified periodic period of time, for example one day, and is not intended to be limited to immediate consecutive administration of each component.

The plant sterol and the soy protein material and/or the isoflavone compound are administered to a human in an amount which is effective to deliver a blood cholesterol concentration decreasing amount of each component to the human. The particular dosage of each component effective to deliver a blood cholesterol concentration decreasing dosage of each component will depend on several factors including the size of the human to which the component is administered, the blood cholesterol concentration of the human to which the component is administered, and the route of administration of the component. Preferably, the plant sterol is administered in a dose of from 500 mg/day to 50 g/day, and more preferably from 1 g/day to 5 g/day, on an ongoing basis, to deliver a blood cholesterol decreasing dose of the plant sterol. Preferably, if administered, the soy protein material is administered in a dose of from 5 g/day to 100 g/day, and more preferably from 10 g/day to 30 g/day, to deliver a blood cholesterol decreasing dose of the soy protein material. Preferably, if administered, the isoflavone is administered in a dose of 10 mg/day to 1000 mg/day, more preferably from 25 mg/day to 200 mg/day, to deliver a blood cholesterol decreasing dose of the isoflavone compound.

When co-administered in amounts effective to individually decrease LDL and total blood cholesterol concentrations, the plant sterol and the soy protein material and/or the isoflavone cooperatively decrease these blood cholesterol concentrations in a human. Plant sterols, soy protein materials, and the isoflavones utilized in the present method decrease LDL and total blood cholesterol concentrations in humans by distinct mechanisms, or distinct combinations of mechanisms which may overlap to some extent. The cholesterol lowering mechanism(s) of each of these materials is believed to interact with such mechanisms of the other materials to accelerate the activity of the cholesterol lowering mechanisms of the other materials. The accelerated activity of the cholesterol lowering mechanisms of the combined cholesterol reducing components causes a collective decrease in LDL and total cholesterol concentrations in the blood which is greater than the decrease in LDL and total cholesterol blood concentrations caused by each of the components separately.

For example, one mechanism by which co-administration of a plant sterol, a soy protein material, and an isoflavone may synergistically decrease LDL and total cholesterol concentrations in the blood combines certain aspects of proposed cholesterol lowering mechanisms of each material. It is known that plant sterols appear to affect the enterohepatic circulation balance between cholesterol and bile acids by preventing absorption of dietary cholesterol in the intestine. This reduces cholesterol feedback in enterohepatic cholesterol circulation regulation, creating a need for cholesterol in the liver to synthesize bile acids. The liver can obtain the necessary cholesterol from the blood through LDL cholesterol receptors in liver cells, which are upregulated by administration of plant sterols, or can synthesize the required cholesterol. Blood cholesterol concentrations drop if the cholesterol required by the liver is removed from the blood.

One known mechanism by which soy protein appears to decrease LDL and total cholesterol concentrations in the blood is by increasing fecal bile acid excretion. Increased fecal bile acid excretion induces the liver to produce more bile acids, utilizing cholesterol as a substrate in the production of the bile acids. As noted above, the liver can obtain cholesterol for the synthesis of bile acids from the blood, lowering blood cholesterol concentrations.

Combined administration of a plant sterol and soy protein in accordance with the present invention may cause a cooperative adjustment of enterohepatic cholesterol homeostasis which results in significantly lower LDL and total cholesterol concentrations in the blood. Inhibition of intestinal absorption of dietary cholesterol by a plant sterol may produce a hepatic deficiency of cholesterol which is relieved in part by pulling cholesterol from the blood. Increased fecal bile acid excretion induced by soy protein may exacerbate the hepatic cholesterol deficiency caused by the plant sterol by increasing the removal of cholesterol from the liver as a bile acid substrate, which is relieved in part by drawing further cholesterol from the blood.

The isoflavones utilized in the present invention are effective to cooperatively lower LDL and total cholesterol concentrations in combination with a plant sterol, or with a plant sterol and a soy protein material, in part because the isoflavones may upregulate or increase the number of hepatic LDL cholesterol-receptors. The isoflavones utilized in the present invention are genistein, daidzein, glycitein, formononetein, biochanin A, and their respective glycosides and glycoside conjugates, which are phytoestrogens that are known to have estrogenic effects in vivo. Estrogen increases the number of hepatic LDL cholesterol receptors, which increases the clearance of LDL cholesterol particles from blood plasma into the liver. In accordance with the present invention, increased upregulation or numbers of hepatic LDL cholesterol receptors induced by the estrogenic effects of the isoflavone(s), in coordination with an increased demand for cholesterol in the liver induced by the plant sterol and/or the soy protein material, may significantly promote the clearance of LDL cholesterol from the blood into the liver.

The method of the present invention, however, is not to be limited to a specific mechanism of action, particularly since there may be several mechanisms by which the co-administered plant sterol, isoflavone(s), and/or soy protein material reduce LDL and total cholesterol concentrations in the blood. For example, in addition to altering cholesterol homeostasis by increasing excretion of bile acids, soy protein may decrease the concentration of LDL and total cholesterol in the blood as result of its high arginine amino acid content, by specific action of the 7S storage unit of the protein, by altering the ratio of serum glucagon to serum insulin which affects cholesterol metabolism in the liver, or by increasing serum free thyroxine concentrations. Plant sterols also function to reduce cholesterol by mechanisms other than inhibition of intestinal absorption of cholesterol since plant sterols have been shown to reduce cholesterol levels by direct injection into the bloodstream.

The present invention is also directed to methods of preventing or minimizing the development of atherosclerosis by co-administering to a human a plant sterol and a soy protein material which is either a soy hypocotyl material or a soy protein material containing at least 49% soy protein by weight and/or at least one isoflavone selected from genistein, daidzein, glycitein, biochanin A, formononetein, and their respective naturally occurring glycosides. The plant sterol is preferably at least one of β-sitosterol, campesterol, stigmasterol, sitostanol, and campestanol. The soy protein material is preferably soy flour, soy grit, soy protein concentrate, or soy protein isolate. The preferred methods of administration and dosages are the same as described above with respect to administering a plant sterol and a soy protein material and/or an isoflavone to lower LDL and total blood cholesterol concentrations.

As described above, the plant sterol and the soy protein material and/or the isoflavones are effective to cooperatively decrease LDL and total blood cholesterol concentrations when administered to a human in amounts sufficient to induce the cholesterol lowering activity of each compound. Elevated levels of LDL cholesterol in the blood have been linked to the development of atherosclerosis, since the LDL cholesterol is the key component in the formation of atherosclerotic plaque. Therefore, the combination of LDL cholesterol lowering plant sterols, soy protein materials, and/or isoflavones are effective to prevent or minimize the development of atherosclerosis.

In a preferred embodiment, the isoflavone is always co-administered in combination with the plant sterol to prevent or minimize the development of atherosclerosis, regardless whether the soy protein material is administered, since the isoflavone provides anti-atherosclerotic activity in addition to lowering the blood concentration of LDL cholesterol. Specifically, these isoflavones provide significant protection against atherosclerosis at the vascular level. The isoflavones—particularly the aglucone isoflavones genistein, daidzein, biochanin A, and formononetein—inhibit oxidation of LDL cholesterol. Oxidation of LDL cholesterol is a key step in the formation of atherosclerotic plaques since oxidation of LDL cholesterol increases its atherogenicity. Some of the isoflavones, particularly genistein, daidzein, and biochanin A, are also tyrosine kinase inhibitors which inhibit the formation of atherosclerotic lesions and thrombin by inhibiting enzymatic tyrosine kinase activity. Therefore, co-administration of plant sterols and at least one of the isoflavones in accordance with the present invention, with or without a soy protein material, prevents or minimizes the development of atherosclerosis, both by cooperatively lowering LDL and total cholesterol levels in the blood and by inhibiting the mechanisms of formation and growth of atherosclerotic plaques.

EXAMPLE 1

Five to fifty men are selected for clinical study. The men are diagnosed with moderate to high hypercholesteremia, e.g. having total blood cholesterol levels of 250 mg/dl or higher. The men are divided into five groups, the first of which receives 30 g of an isoflavone-free isolated soy protein dietary supplement (from which the isoflavones have been removed by alcohol extraction) (the "soy" group), the second of which receives 5 g of a plant sterol dietary supplement which contains the plant sterol β-sitosterol (the "plant sterol" group), the third of which receives 75 mg of an isoflavone dietary supplement which contains the isoflavones genistein and daidzein (the "isoflavone" group), the fourth of which receives a dietary supplement containing 30 g isolated soy protein, 5 g of the plant sterol β-sitosterol, and 75 mg of the isoflavones genistein and daidzein (the "combination" group), and the fifth of which receives no dietary supplement (the "control" group). The diets of the groups are selected to include no further source of isoflavones, plant sterols and soy protein, and no source of estrogen is administered to either of the two groups. The diets are continued for 6 months.

Prior to beginning the diets, the patients are benchmarked as to total and low density lipoprotein blood cholesterol levels. The benchmarked symptoms are measured again for each group after the groups have been on the respective diets for 6 months. The results are compared between members of each group and between the beginning of the study and end of the study for each member. Enhanced activity in reducing LDL and total blood cholesterol levels by the combination of a plant sterol, a soy protein material, and an isoflavone is shown by a greater percent decrease of the LDL or total blood cholesterol levels in the combination group relative the soy group, the plant sterol group, the isoflavone group, and the control group.

Utility of the combination of the plant sterols and soy protein material and/or isoflavones for lowering LDL blood cholesterol concentrations in a human is evidenced by activity in the above example.

EXAMPLE 2

Five to fifty women are selected for clinical study. The women are post-menopausal and have been diagnosed with atherosclerosis, i.e., have been diagnosed with atherosclerotic plaque including stenotic plaque and occlusive plaque. The women are divided into five groups, the first of which receives 30 g of an isoflavone-free isolated soy protein dietary supplement (from which the isoflavones have been removed by alcohol extraction) (the "soy" group), the second of which receives 5 g of a plant sterol dietary supplement which contains the plant sterol β-sitosterol (the "plant sterol" group), the third of which receives 75 mg of an isoflavone dietary supplement which contains the isoflavones genistein and daidzein (the "isoflavone" group), the fourth of which receives a dietary supplement containing 30 g isolated soy protein, 5 g of the plant sterol β-sitosterol, and 75 mg of the isoflavones genistein and daidzein (the "combination" group), and the fifth of which receives no dietary supplement (the "control" group). The diets of the groups are selected to include no further source of isoflavones, plant sterols and soy protein, and no source of estrogen is administered to either of the two groups. The diets are continued for 6 months.

Prior to beginning the diets, the patients are benchmarked as to total blood cholesterol levels; high density and low density lipoprotein blood cholesterol levels; estrogen levels; and degree of stenosis and atherosclerotic plaque in a selected blood vessel to be studied for vascular reactivity non-invasively (e.g., using high resolution ultrasound), such as the superficial femoral artery or the brachial artery. The benchmarked symptoms are measured again for each group after the groups have been on the respective diets for 6 months. The results are compared between members of each group and between the beginning of the study and end of the study for each member. Enhanced anti-atherosclerotic activity of the combination of compounds relative to β-sitosterol, isolated soy protein, the isoflavones genistein and daidzein, and no treatment is shown by either a greater reduction of atherosclerotic plaque and stenosis or the least amount of incremental increase of atherosclerotic plaque or stenosis in the combination group relative to the soy group, the plant sterol group, the isoflavone group, and the control group.

Utility of the combination of the plant sterols and soy protein material and/or isoflavones for preventing or minimizing the development of atherosclerotic plaque in a human is evidenced by activity in the above example.

What is claimed is:

1. A method for lowering blood concentration of total and low density lipoprotein (LDL) cholesterol, in a human comprising:
   co-administering a plant sterol and a soy hypocotyl material to a human to decrease the blood concentration of total and LDL cholesterol in said human, where said plant sterol comprises at least 0.49%, by weight, of the combined weight of the co-administered plant sterol and soy hypocotyl material.

2. The method of claim 1, further comprising administering an isoflavone selected from the group consisting of genistein, daidzein, glycitein, biochanin A, formononetein, and their naturally occurring glycosides and glycoside conjugates.

3. The method of claim 2, wherein said plant sterol, said soy hypocotyl material, and said isoflavone are further administered to minimize the development of atherosclerosis.

* * * * *

UNITED STATES PATENT AND TRADEMARK OFFICE
CERTIFICATE OF CORRECTION

PATENT NO. : 7,285,297 B1
APPLICATION NO. : 10/461751
DATED : October 23, 2007
INVENTOR(S) : Waggle et al.

It is certified that error appears in the above-identified patent and that said Letters Patent is hereby corrected as shown below:

On Title Page

U.S. PATENT DOCUMENTS item 56

Delete "Haynes" and replace therewith --Hayes--.

Delete "Koskenniska" and replace therewith --Koskenniska et al.--.

Delete "10/1998 Waggle et al." and replace therewith --11/1998 Waggle et al.--.

OTHER PUBLICATIONS item 56

Delete "Very Low-Lipoprotein B" and replace therewith --Very Low-Apoprotein B--.

Column 4, line 19, delete "P-sitosterol" and replace therewith --β-sitosterol--.

Signed and Sealed this

Twentieth Day of May, 2008

JON W. DUDAS
*Director of the United States Patent and Trademark Office*